US010799492B2

(12) United States Patent
Sonesson

(10) Patent No.: US 10,799,492 B2
(45) Date of Patent: Oct. 13, 2020

(54) DEUTERATED ANALOGS OF PRIDOPIDINE USEFUL AS DOPAMINERGIC STABILIZERS

(71) Applicant: PRILENIA NEUROTHERAPEUTICS LTD., Herzliya (IL)

(72) Inventor: Clas Sonesson, Gothenburg (SE)

(73) Assignee: PRILENIA NEUROTHERAPEUTICS LTD., Herzliya (IL)

(*) Notice: Subject to any disclaimer, the term of this patent is extended or adjusted under 35 U.S.C. 154(b) by 0 days.

(21) Appl. No.: 16/133,192

(22) Filed: Sep. 17, 2018

(65) Prior Publication Data

US 2019/0015401 A1 Jan. 17, 2019

Related U.S. Application Data

(63) Continuation of application No. 15/960,041, filed on Apr. 23, 2018, now abandoned, which is a continuation of application No. 14/968,522, filed on Dec. 14, 2015, now abandoned, which is a continuation of application No. 13/820,024, filed as application No. PCT/EP2011/064954 on Aug. 31, 2011, now abandoned.

(60) Provisional application No. 61/380,851, filed on Sep. 8, 2010.

(30) Foreign Application Priority Data

Sep. 3, 2010 (DK) .................................. 2010 70385

(51) Int. Cl.
A61K 31/451 (2006.01)
C07D 211/24 (2006.01)
C07D 211/32 (2006.01)
C07B 59/00 (2006.01)

(52) U.S. Cl.
CPC .......... *A61K 31/451* (2013.01); *C07B 59/002* (2013.01); *C07D 211/24* (2013.01); *C07D 211/32* (2013.01)

(58) Field of Classification Search
CPC .. A61K 31/451; C07B 59/002; C07D 211/24; C07D 211/32
See application file for complete search history.

(56) References Cited

U.S. PATENT DOCUMENTS

| 6,903,120 | B2 | 6/2005 | Sonesson et al. |
| 7,417,043 | B2 | 8/2008 | Sonesson et al. |
| 7,923,459 | B2 | 4/2011 | Gauthier et al. |
| 9,006,445 | B2 | 4/2015 | Sonesson et al. |
| 9,012,476 | B2 | 4/2015 | Zimmermann et al. |
| RE46,117 | E | 8/2016 | Sonesson et al. |
| 2006/0135531 | A1 | 6/2006 | Sonesson et al. |
| 2007/0238879 | A1 | 10/2007 | Gauthier et al. |
| 2010/0105736 | A1 | 4/2010 | Wikstrom |
| 2011/0206782 | A1* | 8/2011 | Zhang ................. A61K 31/445 424/722 |
| 2013/0150406 | A1 | 6/2013 | Zimmermann et al. |
| 2013/0197031 | A1 | 8/2013 | Sonesson |
| 2013/0267552 | A1 | 10/2013 | Waters et al. |
| 2014/0088140 | A1 | 3/2014 | Hayden et al. |
| 2014/0088145 | A1 | 3/2014 | Hayden et al. |
| 2014/0315951 | A1 | 10/2014 | Sonesson et al. |
| 2014/0378508 | A1 | 12/2014 | Bassan et al. |
| 2015/0202302 | A1 | 7/2015 | Licht et al. |
| 2015/0209344 | A1 | 7/2015 | Zimmermann et al. |
| 2015/0209346 | A1 | 7/2015 | Hayden et al. |
| 2015/0216850 | A1 | 8/2015 | Hayden et al. |
| 2015/0374677 | A1 | 12/2015 | Schmidt et al. |
| 2016/0166559 | A1 | 6/2016 | Sonesson |
| 2016/0176821 | A1 | 6/2016 | Wu et al. |
| 2016/0243098 | A1 | 8/2016 | Geva et al. |
| 2017/0020854 | A1 | 1/2017 | Licht et al. |
| 2017/0022158 | A1 | 1/2017 | Barel et al. |
| 2018/0055832 | A1 | 3/2018 | Hayden et al. |
| 2018/0235950 | A1 | 8/2018 | Sonesson |
| 2019/0030016 | A1 | 1/2019 | Schmidt et al. |
| 2019/0046516 | A1 | 2/2019 | Russ et al. |
| 2019/0192496 | A1 | 6/2019 | Hayden et al. |
| 2019/0209542 | A1 | 7/2019 | Licht et al. |
| 2019/0231768 | A1 | 8/2019 | Geva et al. |
| 2019/0336488 | A1 | 11/2019 | Hayden et al. |

(Continued)

FOREIGN PATENT DOCUMENTS

| WO | WO 2001/046145 | 6/2001 |
| WO | WO 2001/046146 | 6/2001 |
| WO | WO 2005/012108 | 12/2005 |

(Continued)

OTHER PUBLICATIONS

Dyck et al., 46(2) J. Neurochemistry 399-404 (1986) (Year: 1986).*
De Yebenes et al. "MermalHD study investigators. Pridopidine for the treatment of motor function in patients with Huntington's disease: phase 3; randomised; placebo-controlled trial" Lancet Neurol. 2011;10:1049-57.
Duff et al. "Investigators of the Huntington Study Group. Psychiatric symptoms in Huntington's disease before diagnosis: the predict-HD study" Biological psychiatry. Dec. 15, 2007;62(12)1341-6.
Foster AB. "Deuterium isotope effects in the metabolism of drugs and xenobiotics: implications for drug design" Advances in Drug Research. 1985;14:1-40.

(Continued)

Primary Examiner — Timothy R Rozof
(74) Attorney, Agent, or Firm — Mark S. Cohen; Pearl Cohen Zedek Latzer Baratz LLP

(57) ABSTRACT

The present invention provides novel deuterated analogs of Pridopidine, i.e. 4-(3-methanesulfonyl-phenyl)-1-propyl-piperidine. Pridopidine is a drug substance currently in clinical development for the treatment of Huntington's disease.

In other aspects the invention relates to pharmaceutical compositions comprising a deuterated analog of Pridopidine of the invention, and to therapeutic applications of these analogs.

3 Claims, No Drawings

(56) References Cited

U.S. PATENT DOCUMENTS

| | | |
|---|---|---|
| 2019/0350914 A1 | 11/2019 | Geva et al. |
| 2019/0350915 A1 | 11/2019 | Bassan et al. |

FOREIGN PATENT DOCUMENTS

| | | |
|---|---|---|
| WO | WO 2006/040155 | 4/2006 |
| WO | WO 2007/042295 | 4/2007 |
| WO | WO 2007/058998 | 5/2007 |
| WO | WO 2008/0127188 | 10/2008 |
| WO | WO 2008/0155357 | 12/2008 |
| WO | WO2011/107583 * | 9/2011 |
| WO | WO 2012/028635 | 8/2012 |
| WO | WO 2013/034622 | 3/2013 |
| WO | WO 2018/039475 | 3/2013 |
| WO | WO 20181053275 | 3/2013 |
| WO | WO 2013/152105 | 10/2013 |
| WO | WO 2014/205229 | 12/2014 |
| WO | WO 2015/112601 | 7/2015 |
| WO | WO 2016/003919 | 1/2016 |
| WO | WO 2016/138130 | 9/2016 |
| WO | WO 2017/015515 | 1/2017 |
| WO | WO 2017/015609 | 1/2017 |
| WO | WO 2017/147366 | 8/2017 |
| WO | WO 2018/039477 | 3/2018 |
| WO | WO 2018/053230 | 3/2018 |
| WO | WO 2018/053287 | 3/2018 |
| WO | WO 2018/136600 | 7/2018 |
| WO | WO 2019/036358 | 2/2019 |
| WO | WO 2019/045568 | 3/2019 |
| WO | WO 2019/050775 | 3/2019 |

OTHER PUBLICATIONS

Huang et al. "Analysis and prediction of translation rate based on sequence and functional features of the mRNA" PLos one. Jan. 6, 2011;6(1):e16036.

International Search Report for pct Application No. PCT/EP2011/064954 dated Oct. 17. 2011.

Walker Fo. "Huntington's disease" The Lancet. Jan. 20, 2007;369(9557):218-28.

\* cited by examiner

DEUTERATED ANALOGS OF PRIDOPIDINE USEFUL AS DOPAMINERGIC STABILIZERS

CROSS-REFERENCE TO RELATED APPLICATIONS

This application is a continuation of U.S. patent application Ser. No. 15/960,041, filed on Apr. 23, 2018, now abandoned, which is a continuation of U.S. patent application Ser. No. 14/968,522 filed on Dec. 14, 2015, now abandoned, which is a continuation of U.S. patent application Ser. No. 13/820,024 filed on Apr. 10, 2013, now abandoned, which is a National Phase Application of PCT International Application No. PCT/EP2011/064954, International Filing Date Aug. 31, 2011, claiming the benefit of U.S. Provisional Application No. 61/380,851, filed Sep. 8, 2010, and Denmark Application No. PA 2010 70385 filed Sep. 3, 2010, which are hereby all incorporated by reference.

FIELD OF THE INVENTION

The present invention provides novel deuterated analogs of Pridopidine, i.e. 4-(3-methanesulfonyl-phenyl)-1-propyl-piperidine. Pridopidine is a drug substance currently in clinical development for the treatment of Huntington's disease.

In other aspects the invention relates to pharmaceutical compositions comprising a deuterated analog of Pridopidine of the invention, and to therapeutic applications of these analogs.

BACKGROUND OF THE INVENTION

Deuterium, also called "heavy hydrogen", is a stable isotope of hydrogen with a natural abundance in the oceans of Earth of approximately one atom in 6,500 of hydrogen (~154 ppm). Deuterium thus accounts for approximately 0.0154% (alternately, on a mass basis: 0.0308%) of all naturally occurring hydrogen in the oceans on Earth. The nucleus of deuterium, called a deuteron, contains one proton and one neutron, whereas the hydrogen nucleus contains no neutron.

Deuterium forms bonds with carbon that vibrate at a lower frequency and are thus stronger than C—H bonds. Therefore "heavy hydrogen" versions of drugs may be more stable towards degradation and last longer in the organism. Incorporating deuterium in place of hydrogen thus may improve the pharmacodynamic and pharmacokinetic profiles of drugs, thus modifying the metabolic fate, while retaining the pharmacologic activity and selectivity of physiologically active compounds. Deuterated drugs thus may positively impact safety, efficacy and/or tolerability.

Pridopidine, i.e. 4-(3-methanesulfonyl-phenyl)-1-propyl-piperidine, a dopaminergic stabilizer currently in clinical development for the treatment of Huntington's disease. The compound is described in e.g. WO 01/46145, and in e.g. WO 2006/040155 an alternative method for its synthesis is described.

SUMMARY OF THE INVENTION

The object of the present invention is to provide analogs of Pridopidine with improved pharmacodynamic and pharmacokinetic profiles.

Therefore, in its first aspect the invention provides a partially or fully deuterated analog of 4-(3-methanesulfonyl-phenyl)-1-propyl-piperidine as represented by Formula 1, below.

In another aspect the invention provides a pharmaceutical composition, comprising a therapeutically effective amount of a deuterated analog of 4-(3-methanesulfonyl-phenyl)-1-propyl-piperidine of the invention, or a pharmaceutically acceptable salt thereof, together with at least one pharmaceutically acceptable carrier, excipient or diluent.

Viewed from another aspect the invention relates to the use of the deuterated analog of 4-(3-methanesulfonyl-phenyl)-1-propyl-piperidine of the invention as a medicament, or for the manufacture of a medicament.

In a further aspect the invention provides a method for treatment, prevention or alleviation of a dopamine mediated disorder of a living animal body, including a human, which method comprises the step of administering to such a living animal body in need thereof a therapeutically effective amount of a deuterated analog of 4-(3-methanesulfonyl-phenyl)-1-propyl-piperidine according to the invention, or a pharmaceutically acceptable salt thereof.

Other aspects of the invention will be apparent to the person skilled in the art from the following detailed description and examples.

DETAILED DESCRIPTION OF THE INVENTION

Deuterated Analogs of Pridopidine

In its first aspect the present invention provides deuterated analogs of Pridopidine. The deuterated analog of the invention may be a fully or partially deuterium substituted derivative. The deuterated analog of the invention may in particular be characterised by Formula I

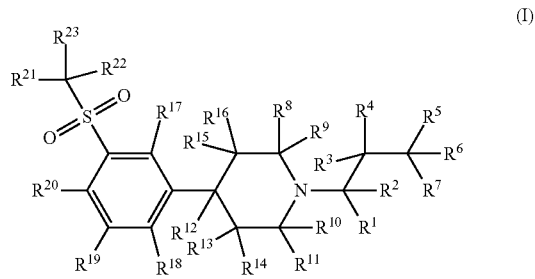

or a pharmaceutically acceptable salt thereof, wherein
at least one of $R^1$-$R^{23}$ represents deuterium (D); and
the remaining of $R^1$-$R^{23}$ represent hydrogen (H).

In the context of this invention, when a particular position is designated as holding deuterium, it is understood that the abundance of deuterium at that position is substantially greater than the natural abundance of deuterium, which is about 0.015%.

In a preferred embodiment the abundance of deuterium at that position is at least 3340 times greater (i.e. at least 50.1% incorporation of deuterium) than the natural abundance of deuterium. In other preferred embodiments of the invention the abundance of deuterium at that position is at least 3500 (52.5% deuterium incorporation), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In a preferred embodiment the deuterated analog of the invention is a compound of Formula I, or a pharmaceutically acceptable salt thereof, wherein
$R^1$-$R^2$ represent deuterium (D); and
all of $R^3$-$R^{23}$ represent hydrogen (H).

In another preferred embodiment the deuterated analog of the invention is a compound of Formula I, or a pharmaceutically acceptable salt thereof, wherein
at least one of $R^1$-$R^7$ represents deuterium (D); and
the remaining of $R^1$-$R^{23}$ represent hydrogen (H).

In a third preferred embodiment the deuterated analog of the invention is a compound of Formula I, or a pharmaceutically acceptable salt thereof, wherein
all of $R^1$-$R^7$ represent deuterium (D); and
all of $R^8$-$R^{23}$ represent hydrogen (H).

In a fourth preferred embodiment the deuterated analog of the invention is a compound of Formula I, or a pharmaceutically acceptable salt thereof, wherein
$R^8$, $R^9$, $R^{10}$ and $R^{11}$ represent deuterium (D); and
all of $R^1$-$R^7$ and $R^{12}$-$R^{23}$ represent hydrogen (H).

In a fifth preferred embodiment the deuterated analog of the invention is a compound of Formula I, or a pharmaceutically acceptable salt thereof, wherein
$R^{12}$ represents deuterium (D); and
all of $R^1$-$R^{11}$ and $R^{13}$-$R^{23}$ represent hydrogen (H).

In a sixth preferred embodiment the deuterated analog of the invention is a compound of Formula I, or a pharmaceutically acceptable salt thereof, wherein
$R^{17}$-$R^{20}$ represent deuterium (D); and
all of $R^1$-$R^{16}$ and $R^{21}$-$R^{23}$ represent hydrogen (H).

Any combination of two or more of the embodiments described herein is considered within the scope of the present invention.

Pharmaceutically Acceptable Salts

The deuterated analog of the invention may be provided in any form suitable for the intended administration. Suitable forms include pharmaceutically (i.e. physiologically) acceptable salts, and pre- or prodrug forms of the deuterated analog of the invention.

Examples of pharmaceutically acceptable salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate, the phthalate, the salicylate, the sorbate, the stearate, the succinate, the tartrate, the toluene-p-sulphonate, and the like. Such salts may be formed by procedures well known and described in the art.

Other acids such as oxalic acid, which may not be considered pharmaceutically acceptable, may be useful in the preparation of salts useful as intermediates in obtaining a deuterated analog of the invention and its pharmaceutically acceptable acid addition salt.

Examples of pharmaceutically acceptable cationic salts of a deuterated analog of the invention include, without limitation, the sodium, the potassium, the calcium, the magnesium, the zinc, the aluminium, the lithium, the choline, the lysinium, and the ammonium salt, and the like, of a deuterated analog of the invention containing an anionic group. Such cationic salts may be formed by procedures well known and described in the art.

The deuterated analog of the invention may be provided in dissoluble or indissoluble forms together with a pharmaceutically acceptable solvent such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

Methods of Preparation

The deuterated analog of the invention may be prepared by conventional methods for chemical synthesis, e.g. those described in the working examples. The starting materials for the processes described in the present application are known or may readily be prepared by conventional methods from commercially available chemicals.

Also one compound of the invention may be converted to another compound of the invention using conventional methods.

The end products of the reactions described herein may be isolated by conventional techniques, e.g. by extraction, crystallisation, distillation, chromatography, etc.

Biological Activity

WO 01/46145, WO 01/46146, WO 2005/121087, WO 2007/042295 WO 2008/127188 and WO 2008/155357 all describe substituted 4-phenyl-N-alkyl-piperazines and 4-phenyl-N-alkyl-piperidines, reported to be modulators of dopamine neurotransmission, and to be useful in treatment of symptoms of various disorders of the central nervous system. The deuterated analog of the invention is considered useful for the same medical indications as described in these publications, and these publications therefore are incorporated by reference.

Neurological indications contemplated according to these publications include the treatment of Huntington's disease and other movement disorders, as well as movement disorders induced by drugs.

Therefore, in a preferred embodiment, the invention relates to the use of the deuterated analog of the invention for use as a medicament for the treatment of Huntington's disease.

Pharmaceutical Compositions

Viewed from another aspect the invention provides deuterated analogs for use as medicaments. Therefore, in another aspect, the invention provides novel pharmaceutical compositions comprising a therapeutically effective amount of the compound of the invention.

While a deuterated analog of the invention for use in therapy may be administered in the form of the raw compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

Pharmaceutical compositions of the invention may in particular be formulated as described in WO 01/46145.

Further details on techniques for formulation and administration may be found in the latest edition of *Remington's Pharmaceutical Sciences* (Maack Publishing Co., Easton, Pa.).

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 1 to about 500 mg of active ingredient per individual dose, preferably of from about 10 to about 100 mg, most preferred of from about 25 to about 50 mg, are suitable for therapeutic treatments. The daily dose will preferably be administered in individual dosages 1 to 4 times daily.

Methods of Therapy

In another aspect the invention provides a method for the treatment, prevention or alleviation of a dopamine mediated disorder of a living animal body, including a human, which method comprises the step of administering to such a living animal body in need thereof a therapeutically effective amount of the deuterated analog of the invention.

In a preferred embodiment the dopamine mediated disorder is Huntington's disease.

EXAMPLES

The invention is further illustrated in the examples below, which in no way are intended to limit the scope of the invention.

Example 1

Preparatory Example 4-(3-Methanesulfonyl-phenyl)-1-propyl-d7-piperidine x HCl 4-(3-Methanesulfonyl-phenyl)-piperidine (0.43 g), CH3CN (4 ml), K$_2$CO$_3$ (0.49 g), and 1-Iodopropane-d7 (0.19 g) are mixed and heated in microwave oven for 30 min at 120° C. The mixture is filtered and evaporated to dryness and purified on silica column using iso-octane:EtOAc (1:1) containing 5% NEt$_3$ as eluent. After evaporation of the fractions with pure product, the residue is re-dissolved in EtOAc and washed with a 10% Na$_2$CO$_3$ solution. The organic phase is separated and dried with Na$_2$SO$_4$, filtered and evaporated to yield pure product (0.33 g). The amine is then converted to the HCl salt, and re-crystallized from EtOH:Et$_2$O. M.p. 198-199° C.

The invention claimed is:

1. A deuterated analogs of 4-(3-methanesulfonyl-phenyl)-1-propyl-piperidine represented as the following Compound D2, Compound D4, and Compound D7:

(D2)

(D4)

(D7)

or a pharmaceutically acceptable salt thereof.

2. A pharmaceutical composition, comprising a therapeutically effective amount of a deuterated analog of 4-(3-methanesulfonyl-phenyl)-1-propyl-piperidine according to claim 1, or a pharmaceutically acceptable salt thereof, together with at least one pharmaceutically acceptable carder, excipient or diluent.

3. The deuterated analog of 4-(3-methanesulfonyl-phenyl)-1-propyl-piperidine according to claim 1, or a pharmaceutically acceptable salt thereof, for use as a medicament.

* * * * *